//  
United States Patent [19]
Leder et al.

[11] Patent Number: 5,175,383  
[45] Date of Patent: Dec. 29, 1992

[54] ANIMAL MODEL FOR BENIGN PROSTATIC DISEASE

[75] Inventors: Philip Leder, Chestnut Hill; William J. Muller, Cambridge, both of Mass.

[73] Assignee: President and Fellows of Harvard College, Cambridge, Mass.

[21] Appl. No.: 312,641

[22] Filed: Feb. 17, 1989

[51] Int. Cl.$^5$ .............................................. C12N 15/00
[52] U.S. Cl. .................................. 800/2; 800/DIG. 1; 435/172.3; 435/317.1; 935/32; 935/111
[58] Field of Search ............................ 800/2, DIG. 1; 435/172.3, 317.1; 935/32, 111

[56] References Cited

U.S. PATENT DOCUMENTS 4,736,866  4/1988  Leder et al. ............................ 800/2

OTHER PUBLICATIONS

Tsukamoto et al., Cell 55: 619–625 (1988).
Brown et al., Cell 46: 1001–1009 (1986).
Stewart et al., Mol. Cell. Biol. 8: 473–479 (1988).
Wilmut et al., New Scientist, Jul. 7, 1988, pp. 56–59.
Van Brunt, BioTechnology 6(10): 1149, 1151, 1152, 1154 (1988).
Wagner et al. (1981) Proc. Nat. Aca. Sci. 78:5016.
Stewart et al. (1982) Science 217:1046.
Constantini et al. (1981) Nature 294:92.
McKnight et al. (1983) Cell 34:335.
Brinster et al. (1983) Nature 306:332.
Palmiter et al. (1982) Nature 300:611.
Palmiter et al. (1982) Cell 29:701.
Palmiter et al. (1983) Science 222:809.
Nusse et al. (1982) Cell 31:99–109.
Peters et al. (1982) J. Virol. 42:880–888.
Dickson et al. (1984) Cell 37:529–536.
Moore et al. (1986) EMBO J., 5:919–924.
Gospodarowicz (1986) Mol. Cell. Endocrinol. 46:187–204.
Folkman et al. (1987) Science 235:442–447.
Slack et al. (1987) Nature 326:197–200.
Delli Bovi et al. (1987) Cell 50:729–737.
Taira et al. (1987) Proc. Nat. Aca. Sci. 84:2980–2984.
Wilkinson et al. (1988) EMBO J. 7:691–695.
Mansour et al. (1988) EMBO, J., 7:2035–2041.
Jakobovits et al., Proc. Natl. Acad. Sci. USA, vol. 83, pp. 7806–7810, (Oct. 1986), Developmental Biology.
Peters et al., Nature, vol. 320 (Apr. 1986), pp. 628–631.

Primary Examiner—Elizabeth C. Weimar
Assistant Examiner—Jasemine C. Chambers
Attorney, Agent, or Firm—Fish & Richardson

[57] ABSTRACT

A male transgenic mouse containing germ cells and somatic cells which contain a recombinant gene which is a vertebrate gene in the int-2/FGF family which is capable of promoting benign prostatic hyperplasia or hypertrophy in said transgenic mouse, said gene being introduced into the mouse, or an ancestor of the mouse, at an embryonic stage.

7 Claims, 7 Drawing Sheets

```
GGATCCAGATGCCCTCTGGATTCATTTGTGACATCTTAGGAGCTTAGGTTGGTCTTCGAGACACAGGGCTGTCCCCTGTAAAGCAGGTTCCATCAGTGACTCCAGGGTTTTAGCAGTTCA       120
GTGGCGTAGTTTTCAGACTGCTTAAGATTTCTCAGGGGCTAGGCGTGGGGCAGAGACCCTGCAGACCCTGCTAGAACAGAGGCCCTGGGAGACAGTTGAGGGTGCTCAGCTGTGGAGGA        240
CATGTGCATTCAGCATGCTGAAGAGGGCCTGCTACCCTGCTAAATGAGGTTCTCAGGGTGGAAAATGTCCCAGTGTGTGCTAGTAATAGCTTCTGTATCGTGGAGGTCCCCACCCAACAC       360
TTCTCAGGATCTCACATCAACAAGGGCTTCCCGCCAGACTCCTCCCAAGAGCTCAGGATCAACTTAGGAACCAATGTTGTGACCCATGCCACAGGGTCCTGAGGCATGCTGAGGGTAGT       480
TGCTGGCCAGGGGACCGTTGGAAGCACAGGATGTGGGGTGGGACCTTTTCTGATACCTCAGGAAGTCCTTCTTCTTTGAGGCCCTTGGCAGATAAGGAACTGAGGTCAAGAGCTCAGGGT      600
CCAGGGAGCTATTCCCTGAACCTGGACTCCCCCTCAGCCTGCCAGTGGGCATGCGGCCCATTGTGGGATCTTCTTTCCGTTCTGTTGCCCTCTGTATCTCCACATTCCTCC               720
CCCTCTCCACTGCTCCTCCTCTTCTTCTTCAGCCAAATCTGTCATCTGCCTCACCCACCTTTATTTCTGTCTCTGCCTAGATTTCCTGTGGCTCTGTAAGCTCTGTGACTCTATTGTCTC     840
TGCTCCTATCTGTGCAGTCCCCTCTGGACCACCGCTGGGACACAGACCACTCCCACTTAAGGTGTGCAAACTTCCTGTGCTACCTTCTGGTCAGTTAGGTAGCTTCGAGCTTAGAGTCCC     960
TGGGCCGTTGGGCCACAAGACTGGACGCCTCGGTGTGAGAAGCACCTGCACGACATCCACCCGGGCTCCCACCGCACCGCCCAATTGCTCTGATTAGCC                            1080
GCCGCCTTTCATGAGCGTTTGTCAGCTAGACTTCCCCGCAAGTTGTTGCCGAGACATCAGTCATCCACAGTCCCATTGTGCACCAGGATTGATGTAAGGCGGGAGGGGGTGACAGGGC        1200
CTGGGGGCCGGTTGCCTCGCTCTATAATTTGTCTGGGGGCGGGGACCTTCAGAGGGCGGGAGGGGGCTCAGGGCGCGCAGGGCGCACGCGGAGGA                                1320
GCGGCGGCCCGACGCTCTGCGCCGGGAGCTGTCGCGCAGGAGCCAGGGACCCCAGGGACCAGCCCCCCGCCCAGTCCCCCGCGCCCTTTTGTTGTCAAGCGCCCTTTCTTCAGAACTGT       1440
GTTCGGCAAAGAAACACGACCCCATTCCTGGGTGAAAATTCAAAGTCTTCTTTCTCCATCTCTTTCTGTCTCTCCACTATCTCTTCCACCCGT                                 1560
CCTTATCTCCATCTCCACCTCTCCACCCTCTCTCCACCTCTCCCTGTCTCCCCTCTTCCCCCGTCTCCCCCTCTTCCCCACCTCTCTCCCCTCCTTCCCCCTCCTCCTAGCCACAGTCGA   1680
GCCCGGCCTGCCGCGCGTGTGCTCCCAGACCCGCTTCGTGAGACCGCGCCTCGCGCAGCCGCTGCGCGGGCGGGATGCCCTGATCTGCCTTCTGCTCTC                           1800
                                                                              MetGlyLeuIleTrpLeuLeuLeu
AGCTTGCTGGAACCTGGCCAACTACGGGGCCCCGGACCGCGACTACGACCCGGGATGCGGGGCGGTGGGCGTTTACGGCCACCTCGGCGGGCGTGGGCGTTTACGGCGCACCGGCCAAGCTCTAC   1920
SerLeuLeuProSerTrpProThrThrProGlyThrArgLeuArgArgAspAlaGlyProGlyThrArgLeuArgArgAspAlaGlyProGlyValGlyValTyrGlyGlyValTyrGlyGlyValAlaProArgArgLysLeuTyr
TGCAGCAAGTACCACCTCCAGTCACCAAGCGGCCCAAGCGGCCCCGTGAACGGCCAGCCTTGAACGGCCAGCCTTGAAACAGCGCCTATAGTAGTCCGGACAGGGAGGGGAGGTGGCGGAAGAGACC   2040
CysAlaThrLysTyrHisLeuGlnLeuHisProSerGlyArgGlyArgValAsnGlySerLeuGluAsnSerAlaTyr
```

```
GATCTGCGGGCTTCCCTGCAAGTGTCTCAGACTGTCTGTGTCCTGAGAAGGGCTGAGGTGCTACATGCAAGCATGTGTTTGTGGGTTCTTATGTCTGCAAATACCCACAAGCATGTGTGT    6600

AGAAGGGTGTTGGTGTATTCCTGAGAACATGTGTGTGAAGCATGCACACAAACTGGCCCTGAACTTTTGACTTCCAGGCCTCTCTGCGCGCACACACACTCGCACTCCTG    6720

TATATGAAGCGTATATGTGTTTCTCGGGAACTGTTTTTATCAGTGAAGTACTTCCTTTGTCTTGCTACCCACCTGCAGGGCTCCAGATCTCCAGACAGCCAACCCTAAGACAGGCC    6840

CAGCTTCCTCTGTATCTCTGTGATGAGAACCTTGGCATAGAGCTGCCCTCACCCTGGGATAGGGCTTATGTTCCCGAACGAGCCACCTCAACAGCTCTGGGAGGAATAGGG    6960

GACTGGGAAGTGTCTGTTGGCTAATATTTAAAACTGACCCAACAGGAGTCTGGGCCACTTCGGGGATCTGTCCCTTAGTCAGAGGCCAGTGGCTTCACACTGGGCGTGGGTTGG    7080

GAGGGAGGCAGGAAACATTCATGTCCTCTCAGTTCCTATCTACCATTTGACCCTGGTTGACACAACAACCTTTTCTGAAAGGTTTTGCTAGATGTGAGTAGCTTACAGAAGGCCATGC    7200

AGGCTCAGGGAAGGCACCACGATAAGCCATTAGTGTCCTGATGAAGAAATTTGGCTGTGAGCTGGGACACACAACAAGCCCCATGGGGAGGAGCACATAGACATTCAGAGCATTC    7320

CACCAGTGAGATTCCATGTGACCTGGGGGCTAAGTCAGGGTGAAGCTTCCACAGCTAAGTGGCTGGAGGCTGCCCTAAAAGCTCAGGAGGCACCGCAAGCAAGCCTTGAAAAACCTTAC    7440

CCACCAGCTTGACCTTAGACTTCTGGCCTTCAGGCCTGTGACAATACATTCCTGCTGTTTAAAGAACCATATGGTTGGTGATGTTTTGTTTCTCGGTCTTTTGTGTTGGTGTTTTT    7560

GTTTGCGGGGTGTGTGTGTGTGTGTGTGTGTGTGTGTGTGTACCAGGTATTGGGTAACCTTAAAAAGAAGACCCCGTAATGCAGGAAGGTGGGGGGGGGGGAGCAGGTCAACTCCCAGAC    7680

GCCAGCTGTGACATTTTTGCCAGCTTCCCTAGCACCATAGTACCAGGTATTGGGTAACCTTAAAAAGAAGACCCCGTAATGCAGGAAGGTGGGGGGGGGGGAGCAGGTCAACTCCCAGAC    7800

TCAAAGTCATCCAAGGAAAATTCTGGATCTTTGTGAGTTCAAGGCTAGCCTGGCCTATATAGAGAATTC
```

FIG. 3d

FIG. 4 ature 300:762–765). Nusse et al., 1982, Cell 31:99–109 and
ANIMAL MODEL FOR BENIGN PROSTATIC DISEASE

BACKGROUND OF THE INVENTION

This invention relates to transgenic animals.

Transgenic animals carry a gene which has been introduced into the germline of the animal, or an ancestor of the animal, at an early (usually one cell) developmental stage. Leder et al. U.S. Pat. No. 4,736,866, hereby incorporated by reference, describes transgenic animals whose germ and somatic cells contain an activated oncogene sequence introduced into the animal at an embryonic stage. Wagner et al. (1981) Proc. Nat. Aca. Sci. 78, 5016; and Stewart et al. (1982) Science 217, 1046 describe transgenic mice containing human globin genes. Constantini et al. (1981) Nature 294, 92; and Lacy et al. (1983) Cell 34, 343 describe transgenic mice containing rabbit globin genes. McKnight et al. (1983) Cell 34, 335 describes transgenic mice containing the chicken transferring gene. Brinster et al. (1983) Nature 306, 332 describes transgenic mice containing a functionally rearranged immunoglobulin gene. Palmiter et al. (1982) Nature 300, 611 describes transgenic mice containing the rat growth hormone gene fused to a heavy metal-inducible metallothionein promoter sequence. Palmiter et al. (1982) Cell 29, 701 describes transgenic mice containing a thymidine kinase gene fused to a metalothionein promoter sequence. Palmiter et al. (1983) Science 222, 809 describes transgenic mice containing the human growth hormone gene fused to a metallothionein promoter sequence.

The existence of potential oncogenes in the DNA of normal somatic cells has been demonstrated by Weinberg, 1981, Biochem. Biophys. Acta 651:25–35 and Bishop et al., 1982, The Molecular Biology of Tumor Viruses, Part III, RNA Tumor Viruses, Chp. 9, Weiss et al., eds., Cold Spring Harbor, N.Y., Cold Spring Harbor Laboratory. Neoplasia is believed to result at least in part from abnormal expression of an endogenous gene, either at abnormally high levels or in some altered or mutated form (Hayward et al., 1981, Nature 290:475–480; Payne et al., 1982, Nature 295:209–214; Reddy et al., 1982, Nature 300:149 $\propto$ 152; Tabin et al., 1982, Nature 300:143–149; Taparowski et al., 1982, Nature 300:762–765). Nusse et al., 1982, Cell 31:99–109 and Peters et al., 1982, J. Virol. 42:880–888 identified two cellular loci, int-1 and int-2, which harbor an MMTV provirus in a majority of virally induced mammary tumors. These loci share no apparent homology with known cellular or viral oncogenes. Dickson et al., 1984, Cell 37:529–536 showed that more than 50% of the mammary tumors arising in BR6 mice contain an acquired MMTV provirus integrated within a defined 25 kb domain of DNA on mouse chromosome 7. Moore et al., 1986, EMBO J. 5:919–924 characterized the int-2 region and isolated a cDNA clone which contains the int-2 gene and which may encode a protein of approximately 27 kD.

There is demonstrable homology between the int-2 gene and members of the family of fibroblast growth factor (FGF) related oncogenes. Basic and acidic FGF have been implicated in endothelial cell proliferation and migration during angiogenesis, in mesodermal induction in Xenopus (Gospodarowicz, 1986, Mol. Cell. Endocrinol. 46:187–204; Folkman and Klagsbrun, 1987, Science 235:442–447; Slack et al., 1987, Nature 326:197–200), and in the formation of nonmammary human tumors (Delli Bovi et al., 1987, Cell 50:729–737 and Taira et al., 1987, Proc. Nat. Aca. Sci. 84:2980–2984).

SUMMARY OF THE INVENTION

In general, the invention features a male transgenic non-human vertebrate animal (preferably a mammal such as a rodent, e.g., a mouse) containing germ cells and somatic cells which contain a recombinant gene which is substantially homologous with a vertebrate gene in the int-2/FGF family which is capable of promoting (i.e., increases the probablility of developing) benign disease of the prostate, e.g., benign prostatic hyperplasia or hypertrophy (respectively. increase in cell number or cell size). The recombinant gene (i e., the gene as it exists prior to introduction into the animal) is introduced into the animal, or an ancestor of the animal, at an embryonic stage (preferably the one-cell, or fertilized oocyte, stage, and generally not later than about the 8-cell stage). The recombinant gene preferably is substantially homologous with (i.e., greater than 50% homologous in terms of encoded amino acid sequence) a naturally occurring, most preferably endogenous, vertebrate gene in the int-2/FGF gene family of murine growth factor encoding genes or their vertebrate counterparts, including the murine acidic or basic fibroblast growth factor (FGF) genes, the murine FGF-5 gene, the murine epidermal growth factor (EGF) gene, the murine insulin-like growth factor-1 and -2 (IGF-1, IGF-2) genes, the murine $\alpha$-transforming growth factor (TGF$\alpha$) gene, or the murine hst/KS3 gene. The non-murine version of each of these genes will in most cases differ to some extent from its murine counterpart. As mentioned -above, it is preferred to use endogenous genes, but genes from other species can also be used, e.g., the human int-2 gene can be introduced into mice. In addition, the recombinant gene can be not only a vertebrate-derived gene or sequence thereof, but also the viral counterpart.

DNA sequences of the genes of the FGF family, aligned to show maximal homology, are shown in FIG. 4. Any recombinant gene or effective sequence thereof derived from this family might be used to produce the transgenic animals of the invention.

There are several means by which transgenic animals can be made. One method involves the use of a transfecting retrovirus containing the transgene. Another method involves directly injecting the transgene into the embryo. Yet another method employs the embryonic stem cell methodology known to workers in this field.

Preferably, transcription of the recombinant gene is under the control of a promoter sequence different from the promoter sequence controlling transcription of the endogenous coding sequence. Transcription of the recombinant gene can also be under the control of a synthetic promoter sequence. Preferably, the promoter sequence controlling transcription of the recombinant gene is active (i.e., can promote gene expression) in the male urogenital tract of the males -of the species to which the male animal of the invention belongs, and is active in prostate tissue. The promoter that controls transcription of the recombinant gene may be of viral origin; examples are promoters sometimes derived from mouse mammary tumor virus (MMTV) and cytomegalovirus (CMV).

Introduction of the recombinant gene at the fertilized oocyte stage ensures that the gene sequence will be present in all of the germ cells and somatic cells of the transgenic "founder" animal. (As used herein, founder (abbreviated "F") means the animal into which the recombinant gene was introduced at the one cell mouse embryo stage.) The presence of the recombinant gene sequence in the germ cells of the transgenic founder animal in turn means that approximately half of the founder animal's descendants will carry the activated recombinant gene sequence in all of their germ cells and somatic cells. Introduction of the recombinant gene sequence at a later embryonic stage might result in the gene's absence from some somatic cells of the founder animal, but the descendants of such an animal that inherit the gene will carry the activated recombinant gene in all of their germ cells and somatic cells.

The animals of the invention can be used as models to test for agents potentially useful in the treatment of benign prostatic hyperplasia or hypertrophy in humans; benign prostate hyperplasia is a serious medical condition affecting a large percentage of the human male population at some time. The agent to be tested can be administered to an animal of the invention and abnormal prostatic growth monitored. The animals of the invention can also be used to test a material suspected of promoting benign prostatic hypertrophy or hyperplasia, by exposing the animal to the material and determining accelerated abnormal growth as an indicator of benign hyperplasia. These tests can be extremely sensitive because of the propensity of the transgenic animals of the invention to develop abnormal tissue growth. This sensitivity will permit potential drug treatments or suspect materials to be tested in much smaller amounts than the amounts used currently in the study of abnormal tissue growth, and thus will minimize one source of criticism of current methods, that their validity is questionable because the amounts of the tested material used is greatly in excess of amounts to which humans are likely to be exposed. Until now, there have been no satisfactory animal models in which benign prostatic hypertrophy or hyperplasia can be made to occur in a reliable and predictable fashion in a substantial proportion of animals.

The animals of the invention can also be used as a source of cells for cell culture. Cells from the animals may advantageously exhibit desirable properties of both normal and transformed cultured cells; i.e., they will be normal or nearly normal morphologically and physiologically, but can, like cells such as NIH3T3 cells, be cultured for long, and perhaps indefinite, periods of time. Further, where the promoter sequence controlling transcription of the recombinant gene sequence is inducible, cell growth rate and other culture characteristics can be controlled by adding or eliminating the inducing factor.

Other features and advantages of the invention will be apparent from the description of the preferred embodiments thereof, and from the claims.

DESCRIPTION OF THE PREFERRED EMBODIMENTS

The drawings will first briefly be described.

Drawings

FIG. 3 (a)-(d) is the DNA sequence of the c-int-2 gene (from Moore et al., 1986, EMBO J. 5:919).

FIG. 4 is a comparison of amino acid sequences of proteins which are members of the FGF family, aligned to show maximal homology.

INT-2 GENE EXPRESSION

The murine int-2 gene was originally identified as a common integration site for MMTV and is implicated in mammary tumorigenesis in certain strains of mice (Peters et al., 1983, Cell 33:364-377; Dickson et al., 1984, Cell 37:529-536). The int-2 gene is not detectably expressed in normal mammary glands, yet transcripts accumulate in many mammary tumors as a consequence of proviral insertion 5' or 3' of the int-2 gene (Dickson et al., 1984, supra; Moore et al., 1986, supra; Peters et al., 1986, Nature 320:628-631). Expression of int 2 is highly restricted in normal uninfected cells; int-2 specific transcripts are found in normal mouse embryos of around 7.5 days of gestation, but are not found in normal adults tissues (Dickson et al., 1984, supra; Jakobovits et al., 1986, Proc. Nat. Aca. Sci. 83:7806). Thus, a role may exist in early mouse development for the int-2 gene product.

MMTV-int 2 Fused Genes

Figure 1:
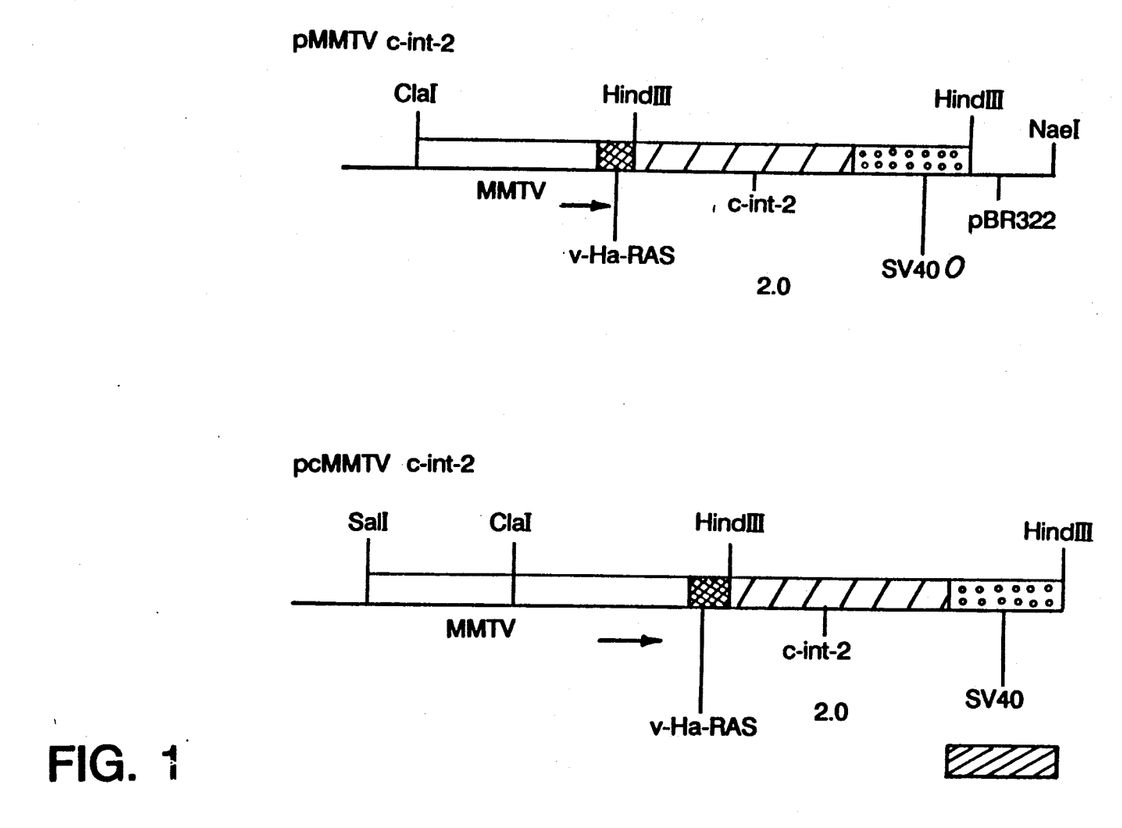
FIG. 1 is a diagrammatic representation of the MMTV c-int 2 coding inserts from the plasmids constructed in FIG. 2.

An expressible proto-oncogene of the invention was constructed by fusing int-2 coding sequences to viral regulatory sequences; in this case, the mouse int-2 gene (c-int-2) and the MMTV long terminal repeat (LTR) were fused, according to conventional techniques, described in Maniatis et al. (1982) Molecular Cloning: A Laboratory Manual (Cold Spring Harbor Laboratory). FIG. 1 illustrates the mouse c-int-2 gene fusion; restriction sites are shown; solid arrows below the constructions represent the promoter in the MMTV LTR; and the int-2 gene is shown by the boxed region labeled c-int 2. The size (in Kb) of the major fragment produced by digestion with HindIII that will hybridize with the int-2 probe is given for each construction. These MMTV-int-2 constructions were made as follows.

An MMTV DNA fragment from the plasmid pA9, described in Huang et al. (1981) Cell 27:245, including the region required for glucocorticoid control, the MMTV promoter, and the cap site, is carried on the plasmid pMMTVneu NT (Muller et al., 1988, Cell 54:105). In the pA9 construct, this control region directs expression of an inducible protein called p21; the neu gene in pMMTVneu NT is controlled by this same region and is also inducible.

Figure 2:
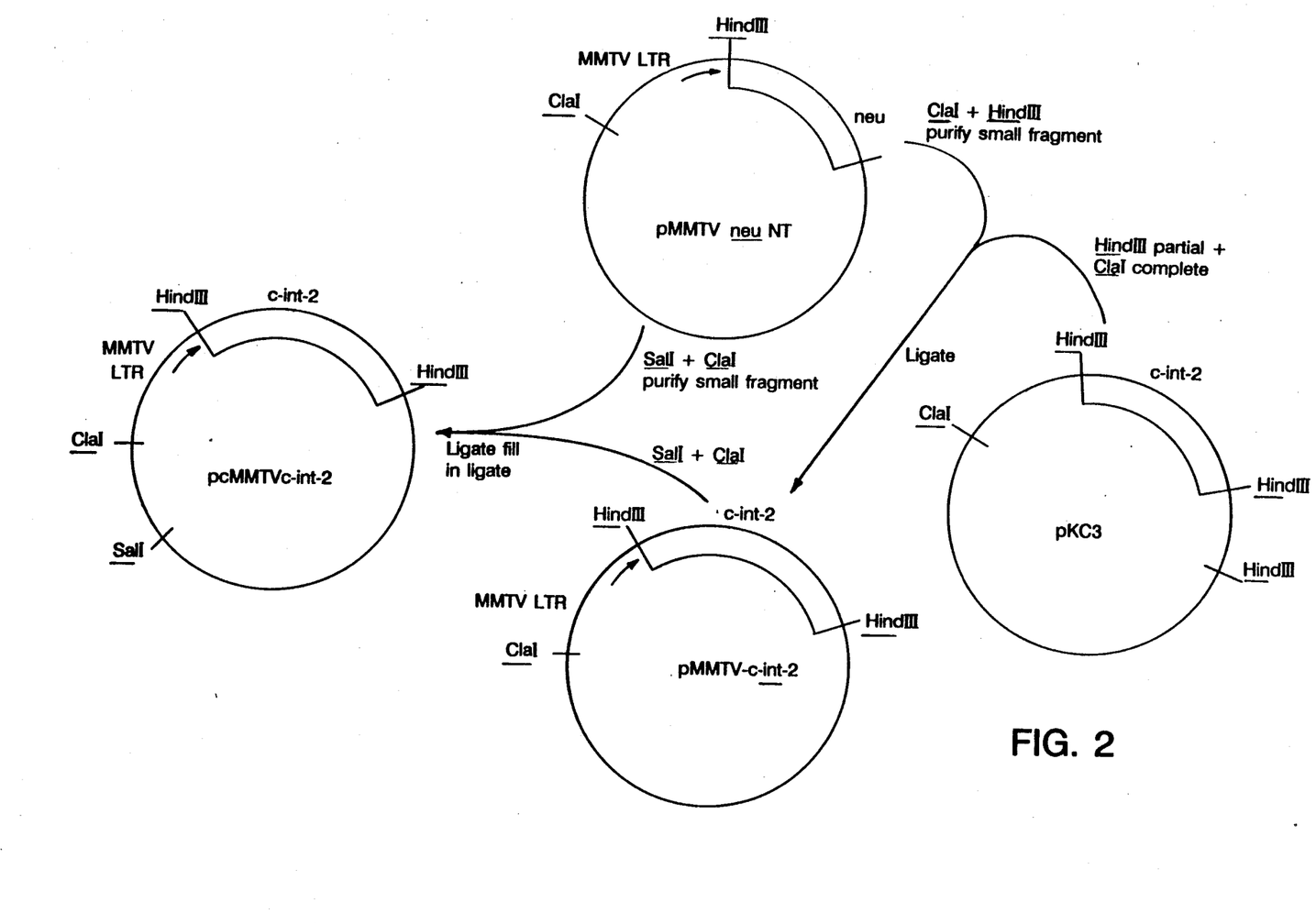
FIG. 2 is a diagrammatic representation of construction of the MMTV-c-int 2-containing plasmids, pMMTVc-int 2 and pcMMTVc-int-2.
Figure 3A:
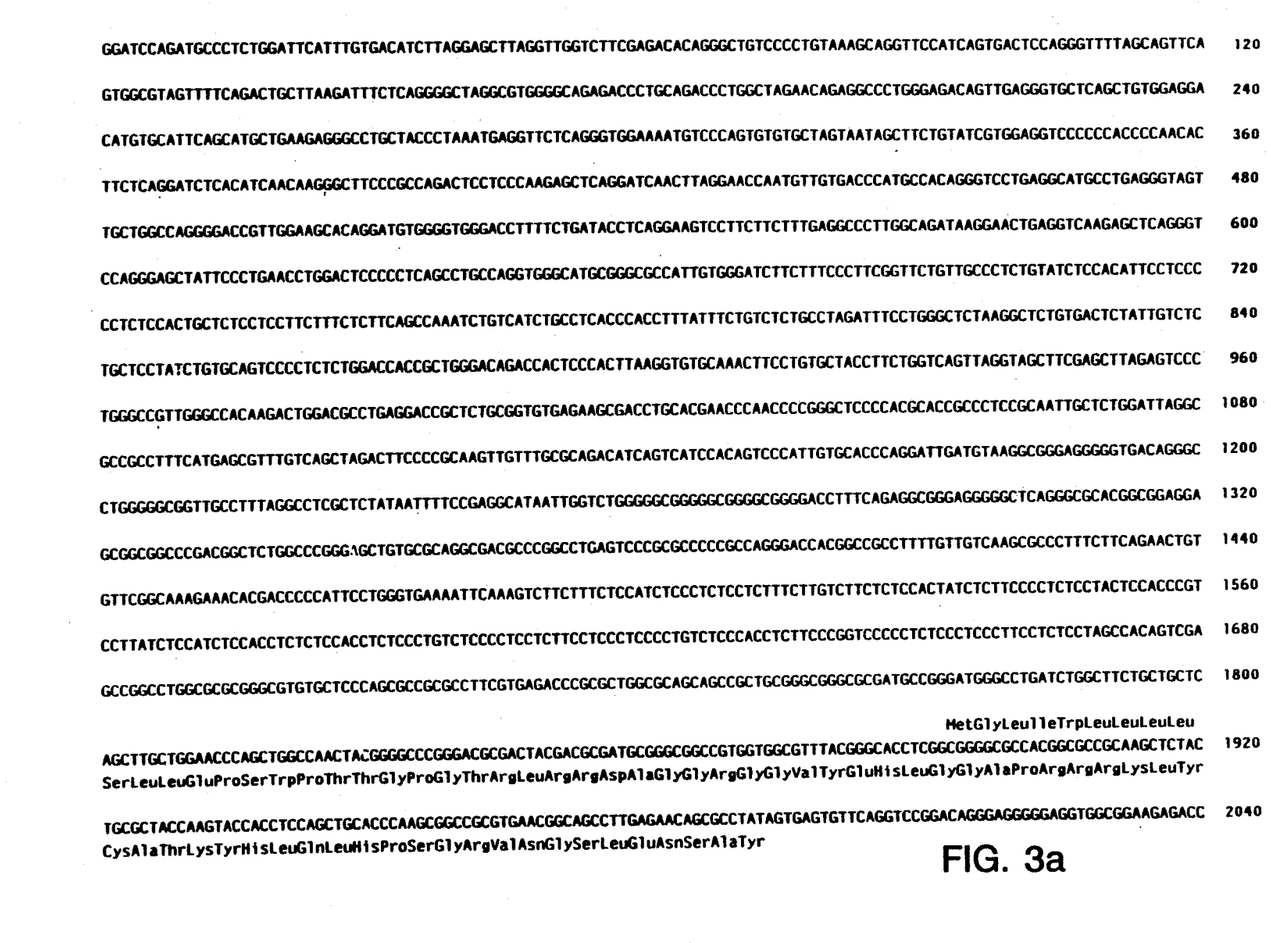
Figure 3B:
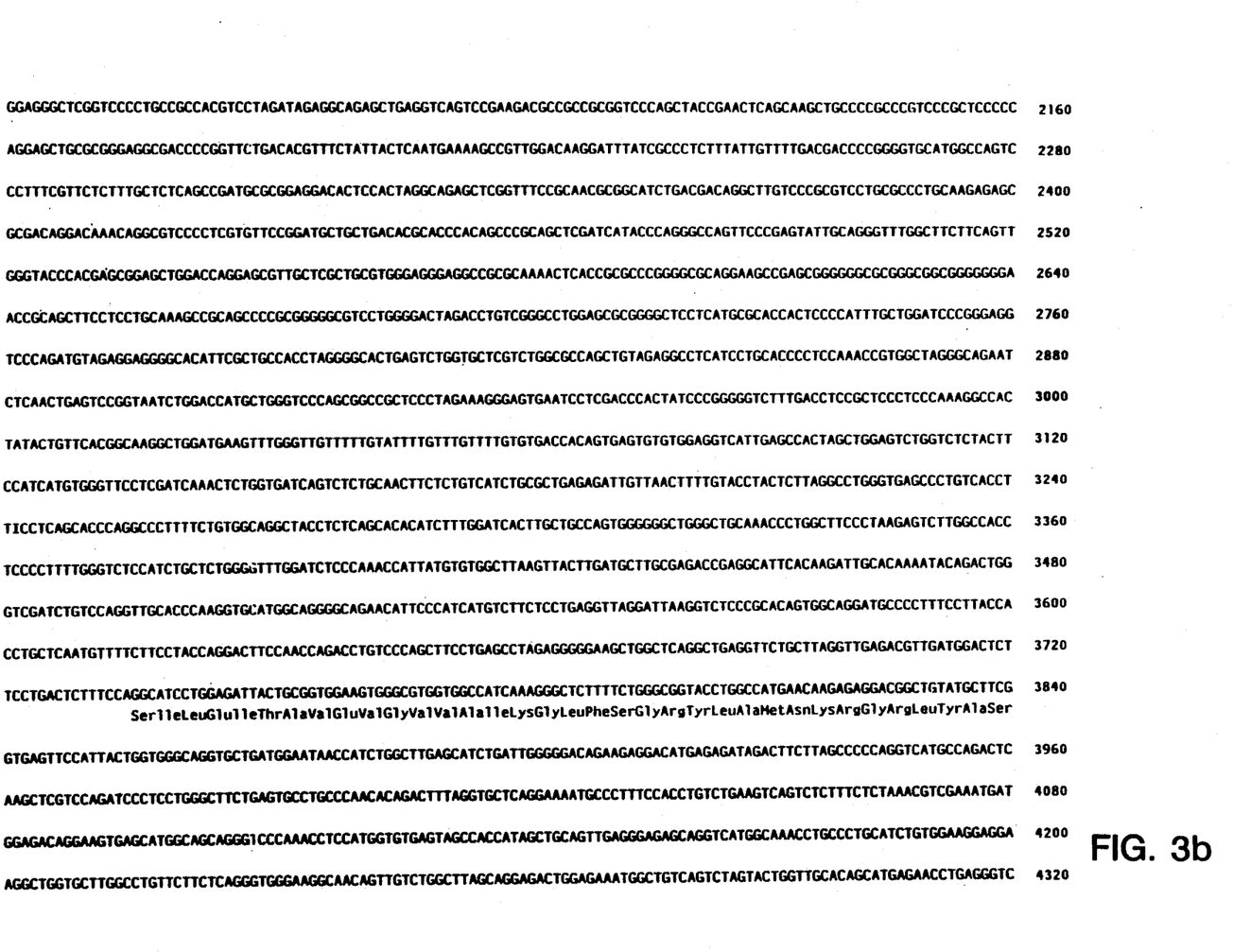
Figure 3C:
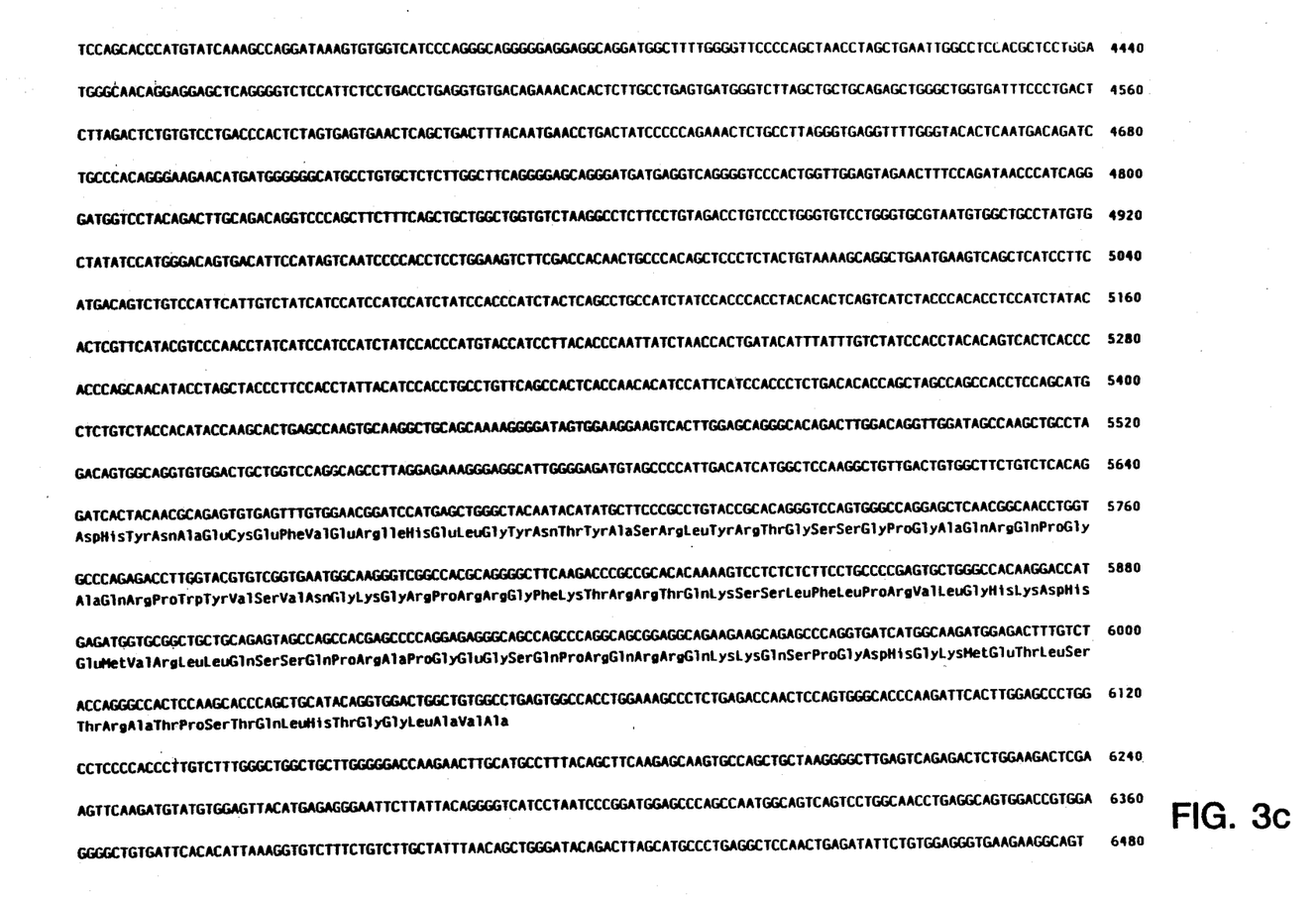
Figure 3D:
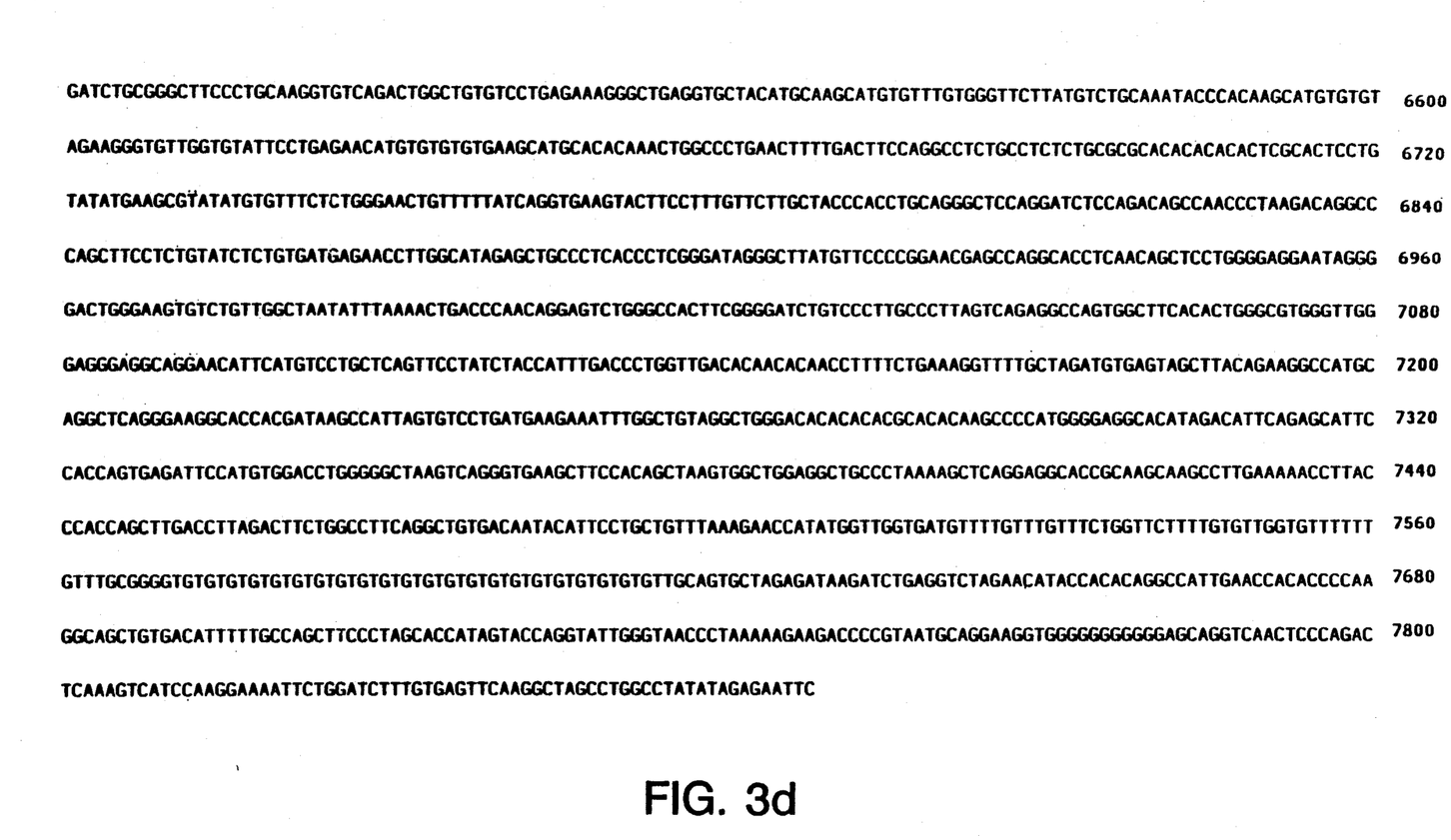

FIG. 2 illustrates the construction of the c-int-2 gene fusions. The mouse c-int-2 gene, whose DNA sequence is given in FIG. 3, was obtained from plasmid pKC3 (Moore et al., 1986, E.M.B.O. Journal 5:919). The c-int 2 coding plasmid pKC3 was partially digested with HindIII and completely digested with ClaI, and then ligated to a ClaI +HindIII restriction fragment from pMMTVneu NT, bearing the MMTV regulatory sequences. Recombinant DNA clones containing the MMTV LTR fragment upstream of and directing the expression of the c-int-2 gene were verified by restriction enzyme analysis of plasmid DNA. The MMTV-c-int-2 fusion gene can be inducibly expressed in this construct.

pMMTVc-int-2 does not contain MMTV LTR sequences upstream of the ClaI site; therefore, a second construct was made which contains the entire MMTV LTR linked to c-int-2 sequences. As shown in FIG. 2, the MMTV LTR was isolated on a SalI +ClaI restriction fragment derived from pMMTVneu NT, and inserted into the unique ClaI site of pMMTVc-int-2 by ligation of the cohesive ClaI ends, treatment of the non-ligated, noncohesive ends with the Klenow fragment of DNA Polymerase I, and blunt end ligation, according to conventional techniques. A plasmid was produced, pcMMTVc-int-2, which contains the entire MMTV LTR fused to the c-int-2 cDNA. In order to ensure proper expression of these gene fusions, these constructs also contain SV40-derived splicing and polyadenylation signals (designated "SV40" in FIGS. 1 and 2) downstream of the c-int 2 coding region.

These constructions were verified by multiple restriction enzyme digestions and were found to be free of detectable rearrangements.

Production of Transgenic Mice Containing MMTV-c-int-2 Fusions

The above MMTV-int-2 gene fusions were incorporated into the germ cells of mice as follows. pMMTVc-int-2 DNA was prepared for injection by digestion with 4 units each of ClaI and NaeI per $\mu$q of DNA for 1 hour at 37° C., electrophoresed through a 1% agarose gel, and purified as described by Sinn et al (1987) Cell 49:465. pcMMTVc-int 2 DNA was treated identically except that it was digested only with NaeI. Each DNA segment was separately injected into the pronuclei of fertilized one-cell mouse eggs derived from the FVB/NHd inbred strain (Taconic Laboratory, Germantown, NJ); this resulted in about 500 copies of linearized plasmid per pronucleus. Following micro-injection, viable eggs were transferred to the oviducts of pseudopregnant Swiss Webster mice (Taconic Farms, Germantown, PA), as described by Wagner et al. (1981) Proc. Nat. Aca. Sci. 78:5016. Mice were housed in an environmentally controlled facility maintained on a 10 hour dark: 14 hour light cycle. The eggs in the foster females were allowed to develop to term.

Analysis of Transgenic Mice

At four weeks of age, each pup born was analyzed using DNA taken from the tail in a Southern hybridization. In each case, DNA was extracted from 1.5 cm sections of tail, as described by Davis et al. (1980) Meth. Enzymol. 65:405, with the modification that one chloroform extraction was performed prior to ethanol precipitation. The nucleic acid pellet was resuspended in 200 $\mu$l of 10 mM Tris-Cl pH 7.4, 0.1 mM EDTA, and 10 $\mu$q was digested with BamHI, electrophoresed through 1.0% agarose, and transferred to nitrocellulose, as described by Southern (1975) J. Mol. Biol. 98:503. Filters were hybridized overnight to probes in the presence of 10% dextran sulfate and washed twice in 2X SSC, 0.1% SDS at 64° C. The c-int-2 DNA probe was labeled by nick-translation with $^{32}$P dCTP, according to Rigby et al., 1977, J. Mol. Biol. 113:237.

The Southern hybridization indicated that four founder mice had retained an MMTV int-2 fusion. Two founder animals, the NR-F female and the NS-F male, had integrated the int-2 gene from the pMMTV-c-int2 construct, and the other two, the NW-F male and the NX-F male, had integrated the int-2 gene from the pcMMTV-c-int2 construct. The NR-F transgenic female gave both male and female offspring containing the MMTV-c-int-2 gene fusion. Because they exhibited prostate hyperplasia, the NS-F and NW-F male transgenic offspring were sterile.

Transcription of the MMTV-c-int-2 Gene in Transgenic Mice

Transcription of the newly acquired genes in tissues was determined by extracting RNA from the tissues and assaying the RNA in a ribonuclease (RNAase) protection procedure as follows. The excised tissue was rinsed in 5.0 ml cold Hank's buffered saline and total RNA was isolated by the method of Chrigwin et al. (1979) Biochemistry 18:5294, using the CsCl gradient modification. RNA pellets were washed twice by reprecipitation in ethanol and quantitated by absorbance at 260 nm. An appropriate single stranded, uniformly labeled RNA probe was prepared as described by Melton et al. (1984) Nucl. Acids Res. 12:7035. To test for transcription of the pMMTV-c-int-2 gene fusions of FIG. 1, for example, a probe illustrated as a solid box below the construct was used. Transcription from the MMTV promoter of the constructs will protect the probe and be revealed as two bands, approximately 200 and 125 base pairs long, corresponding to a transcribed noncoding SV40 sequence used in the construction of the MMTV-c-int-2 fusion genes; transcription of the endogenous c-int-2 gene, if it is expressed in the cell, will produce RNA that will not be protected, since the SV40 sequence is not present in normal cells. The RNAase protection assay is described as follows.

Labelled single-stranded probe fragments were isolated on 8M urea 5% acrylamide gels, electroeluted, and hybridized to total RNA in a modification of the procedure of Berk et al. (1977) Cell 12, 721. The hybridization mixture contained 50,000 cpm to 100,000 cpm of probe (SA = $10^8$ cpm/$\mu$g), 10 $\mu$g total cellular RNA, 50% formamide, 500 mM NaCl, 20 mM Tris pH 7.5 1 mM EDTA, as described in Melton et al. (1984, supra). Hybridization temperatures were varied according to the GC content in the region of the probe expected to hybridize to mRNA. The hybridizations were terminated by the addition of 1500 units of RNAase A and RNAase T$_1$ (Sigma, St.Louis, MO). RNAase digestions were carried out at 37° C. for 15 min. The samples were then ethanol-precipitated and electrophoresed on thin 8M urea 5% acrylamide gels.

The tissues analyzed were prostate, seminal vesicle, vas deferens, and salivary gland.

10$\mu$g of total RNA from each of these tissues was analyzed The antisense probe used in this analysis is transgene specific and yields the same two protected fragments described above, corresponding to the SV40 region of the MMTV-c-int-2 fusion genes. Table I shows results of RNase protection assays of MMTV-int-2 fusion gene specific transcripts in RNA from different tissue sources. Relative RNA levels are indicated by +(low), + +(intermediate), or + + +(high). The results in presented in Table I show that transgene specific transcripts were detected in the prostate, seminal vesicles, vas deferens, and salivary glands derived from the NS-F animal. Table I also shows that the male NR transgene carrier (TG, NR, or transgene NR) expressed the transgene in the prostate and salivary glands, while the female transgenic NR animals expressed abundant levels of transgene specific transcripts in the mammary gland. In the MMTV/c-neu strain, TG.NF, mammary gland specific expression of the c-neu oncogene initially results in a lactation defect followed by the synchronous appearance of tumors involving mammary glands in the transgenic mouse.

Expression of the MMTV/int 2 fusion gene in the prostate gland in males derived from two independant transgenic lines (100% of NR males and the NS-F male) resulted in uniform enlargement of this gland. This enlargement was closely associated with low fertility exhibited by male transgenic animals. Histological analyses of the enlarged prostates revealed tissue hyperplasia and hypertrophy without evidence of malignant transformation; the prostate growths were shown to be benign by their inability to grow after reimplantation into nu/nu mice.

Use 7 Transgenic animals of the invention can be used for testing agents that may cure the disease, or relieve its symptoms, or for testing for agents that may promote prostate disease.

Treatment

Transgenic animals of the invention are most useful as animal models for agents and procedures useful in treating or diagnosing benign prostatic hyperplasia or hypertrophy in humans. Treatments that potentially cure this disease, or relieve its symptoms, may be tested first in a transgenic animal which exhibits benign prostatic hyperplasia or hypertrophy by administering the potential treatment to the animal and observing the effects, and comparing the treated animals to untreated controls.

Testing

The animals of the invention can be used to test a material suspected of promoting prostate hyperplasia as follows. If the animals are to be used to test materials thought to be only weakly effective in promoting abnormal tissue growth, the transgenic animals most susceptible to developing abnormal growth are selected, by exposing the animals to a low dosage of a known agent, and selecting those which first develop benign prostatic hyperplasia or hypertrophy. The selected animals and their descendants are used as test animals by exposing them to the material suspected of promoting abnormal tissue growth and determining this growth as an indicator of benign prostatic disease. Less sensitive animals are used to test more strongly suspect materials. Animals of the desired sensitivity can be selected by varying the type and concentration of a known agent, e.g. a carcinogen or a hormone, used in the selection process. When extreme sensitivity is desired, the selected test animals can consist of those which spontaneously develop benign prostatic hyperplasia or hypertrophy.

Tissue Culture

The transgenic animals of the invention can be used as a source of cells for cell culture. Tissues of transgenic animals are analyzed for the presence of the activated recombinant gene, either by directly analyzing DNA or RNA, or by assaying the tissue for the protein expressed by the gene. Cells of tissues carrying the gene can be cultured, using standard tissue culture techniques, and used, e.g., to study the causes of benign prostatic disease at the cellular and tissue levels.

Other Embodiments

Other embodiments are within the following claims. For example, any species of transgenic animal can be employed. In some circumstance, for instance, it may be desirable to use a species, e.g., a primate such as the rhesus monkey, which is evolutionarily closer to humans than mice. Non-mammals, e.g., birds such as chickens, can be used as well.

TABLE 1

| Transgene Expression in MMTV/c-int-2 Mice | | | | | | |
|---|---|---|---|---|---|---|
| | | | | Tissue | | |
| Strain | Sex | Mammary | Salivary | Prostate | Seminal vesicles | Vas Deferens |
| NS-F | male | ND | + | ++ | +++ | ++ |
| TG.NR | female | +++ | + | ND | ND | ND |
| | male | ND | + | ++ | + | − |

We claim:

1. A male transgenic mouse, whose germ cells and somatic cells contain an int-2 gene which is operably linked to a promoter effective for the expression of said gene in the urogenital tissues of said mouse and effective for the promotion of benign prostatic hyperplasia or hypertrophy in said mouse, said gene being introduced into said mouse, or an ancestor of said mouse, at an embryonic stage.

2. The mouse of claim 1, wherein a chromosome of said mouse includes an endogenous coding sequence substantially the same as the coding sequence of said int-2 gene.

3. The mouse of claim 2, wherein said int-2 gene has integrated into a chromosome of said mouse at a site different from the location of said endogenous coding sequence.

4. The mouse of claim 2, wherein transcription of said int-2 gene is under the control of a promoter sequence different from the promoter sequence controlling the transcription of said endogenous coding sequence.

5. The mouse of claim 4, wherein said promoter sequence controlling transcription of said int-2 gene is inducible.

6. The mouse of claim 1, wherein transcription of said int-2 gene is under the control of a viral promoter sequence.

7. The mouse of claim 6, wherein said viral promoter sequence comprises the sequence of the MMTV promoter.

* * * * *